(12) United States Patent
Kobayashi et al.

(10) Patent No.: US 11,266,452 B2
(45) Date of Patent: Mar. 8, 2022

(54) ORTHOPEDIC CABLE RETENSION DEVICE AND METHODS OF PRODUCTION AND USE THEREOF

(71) Applicant: DePuy Synthes Products, Inc., Raynham, MA (US)

(72) Inventors: Kenneth Kobayashi, West Chester, PA (US); Troy Probst, West Chester, PA (US); Eric Lui, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 16/891,927

(22) Filed: Jun. 3, 2020

(65) Prior Publication Data
US 2021/0378724 A1   Dec. 9, 2021

(51) Int. Cl.
| A61B 17/56 | (2006.01) |
|---|---|
| A61B 17/58 | (2006.01) |
| A61B 17/82 | (2006.01) |
| A61F 2/30 | (2006.01) |
| A61B 17/00 | (2006.01) |
| A61B 17/68 | (2006.01) |

(52) U.S. Cl.
CPC .... *A61B 17/82* (2013.01); *A61B 2017/00862* (2013.01); *A61B 2017/00867* (2013.01); *A61B 2017/564* (2013.01); *A61B 2017/681* (2013.01)

(58) Field of Classification Search
USPC .............................. 606/74, 103, 326, 327, 78
See application file for complete search history.

(56) References Cited

U.S. PATENT DOCUMENTS

| 5,766,218 | A | 6/1998 | Arnott |
|---|---|---|---|
| 5,797,915 | A | 8/1998 | Person, III et al. |
| 8,613,755 | B1 | 12/2013 | Foerster |
| 9,131,968 | B2 | 9/2015 | Cavallazzi et al. |
| 2002/0177853 | A1 | 11/2002 | Chervitz et al. |
| 2010/0274249 | A1* | 10/2010 | Dell'oca ................ A61B 17/82 606/74 |
| 2010/0318137 | A1 | 12/2010 | Stucki et al. |

FOREIGN PATENT DOCUMENTS

WO   2015026359 A1   2/2015

OTHER PUBLICATIONS

Sears, et al.; "Increased Fracture Site Compression Using Shape Memory Alloy for Cerclage Wire Fixation," 47th Annual Meeting, Orthopaedic Research Society, Feb. 25-28, 2001, San Francisco, CA. p. 0994.
International Searching Authority in PCT/IB2021/054012, dated Aug. 5, 2021, filed May 11, 2021.
Written Opinion of the International Searching Authority in PCT/IB2021/054012, dated Aug. 5, 2021, filed May 11, 2021.

* cited by examiner

*Primary Examiner* — Sameh R Boles
(74) *Attorney, Agent, or Firm* — Dunlap Codding, P.C.

(57) ABSTRACT

Retension compression devices are disclosed that are formed of an elastic material that is compressed prior to use. The retension compression devices are designed for utilization with orthopedic cable to maintain tension in the orthopedic cable upon placement periprosthetically. Assemblies, systems, and kits containing same, as well as methods of production and use thereof, are also disclosed.

14 Claims, 5 Drawing Sheets

ORTHOPEDIC CABLE RETENSION DEVICE AND METHODS OF PRODUCTION AND USE THEREOF

CROSS REFERENCE TO RELATED APPLICATIONS/INCORPORATION BY REFERENCE STATEMENT

Not Applicable.

STATEMENT REGARDING FEDERALLY SPONSORED RESEARCH OR DEVELOPMENT

Not Applicable.

BACKGROUND

Peri-prosthetic fractures are common injuries that may be very difficult to treat; for example, a previously placed implant may interfere with the healing or placement of other bone fixation elements. One system of treating a peri-prosthetic fracture loops a cable around the bone to secure a fractured portion of the bone. These cerclage systems rely on passing or wrapping a cable around two segments of bone and then tensioning, crimping, and cutting the cable to squeeze the bone segments together. Cerclage systems are often used in conjunction with implants (i.e., prostheses and plates, as well as their associated hardware) that may be positioned along the fractured bone to provide stability to the bone during healing.

However, as these orthopedic cables are maintained under tension against portions of the bone, the cable can start to cut into the bone over time. This causes the cable, which is "squeezing" the bone together, to become loose. The slack that is created can affect the placement of all of the components of the system and may decrease the success of the system and the healing process as a whole.

Therefore, there is a need in the art for new and improved devices and methods of using same to increase stability of periprosthetic devices utilized for fracture fixation. It is to such devices, as well as methods of producing and using same, that the present disclosure is directed.

Figure 1:
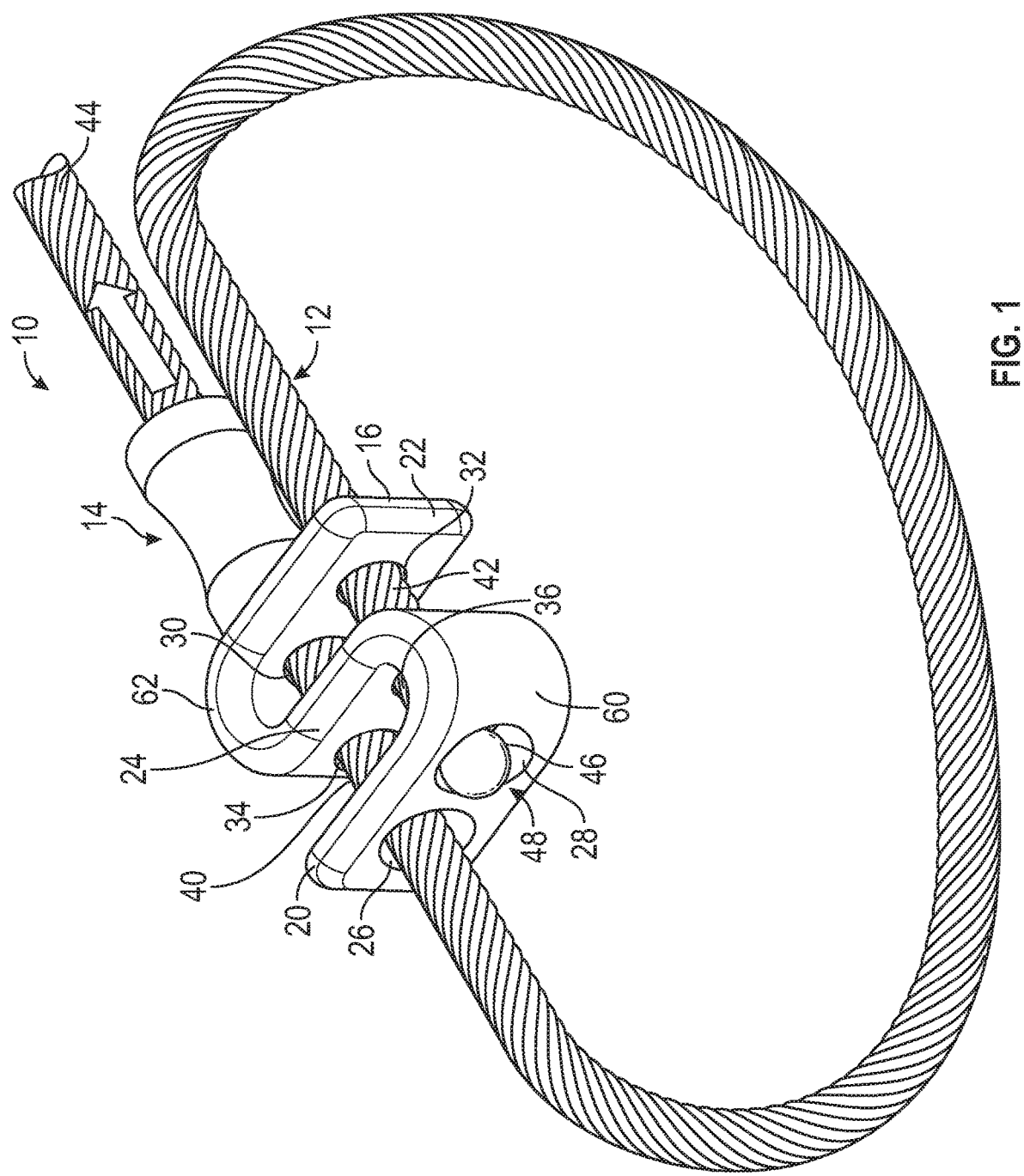
FIG. 1 is a perspective view of a non-limiting embodiment of an orthopedic cable/crimp/retension device assembly constructed in accordance with the present disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure.

DETAILED DESCRIPTION

Before explaining at least one embodiment of the present disclosure in detail by way of exemplary language and results, it is to be understood that the present disclosure is not limited in its application to the details of construction and the arrangement of the components set forth in the following description. The present disclosure is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the medical procedures and techniques of, surgery, anesthesia, wound healing, and infectious control described herein are those well-known and commonly used in the art. Standard techniques are used for infection diagnostic and therapeutic application.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles, compositions, kits, and/or methods disclosed herein can be made and executed without undue experimentation in light of the present disclosure. While the articles, compositions, kits, and/or methods have been described in terms of particular embodiments, it will be apparent to those of skill in the art that variations may be applied to the articles, compositions, kits, and/or methods and in the steps or in the sequence of steps of the methods described herein without departing from the concept, spirit, and scope of the present disclosure. All such similar substitutes and modifications apparent to those skilled in the art are deemed to be within the spirit, scope, and concept of the present disclosure as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

As used herein, the phrases "associated with" and "coupled to" include both direct association/binding of two moieties to one another as well as indirect association/binding of two moieties to one another. Non-limiting examples of associations/couplings include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety, for example.

As used herein, the term "patient" or "subject" is meant to include all organisms, whether alive or dead, including any species having soft tissues and bones. For example, a method according to the inventive concepts disclosed herein may be used to apply a retension device to a living human, horse, cow, sheep, cat, dog, and the like.

The term "ambient temperature" as used herein refers to a temperature of the air surrounding a skin of a subject. That is, the "ambient temperature" is the temperature of the subject's environment. When located indoors, the ambient temperature is typically in a range of from about 60° F. to about 80° F. However, when the subject is located outdoors, the ambient temperature may be greater than or less than the above range. For the devices taught herein to be effective upon application to the skin, the ambient temperature should be sufficiently below body temperature (i.e., 98.6° F.) at the time of application of the device to the skin; otherwise, the retension device will not adequately function in accordance with the present disclosure.

The present disclosure is directed to a device for use with an orthopedic cable that may be disposed/wrapped about a bone, either alone or in combination with an implant (such as, but not limited to, a plate or prosthesis). Over time, the orthopedic cable wrapped about the bone tends to cut into bone, and this causes the orthopedic cable to naturally lose its tension about the bone/implant, which introduces slack into the assembly and allows the plate/prosthesis to lift off the bone. The disclosed device can automatically retension the orthopedic cable if it begins to cut into the bone, thus preventing any slack from being introduced into the assembly and retaining the desired positioning of the plate/prosthesis upon or within the bone. The retensioning characteristic is obtained by forming at least a portion of the device from an elastic material and extending the two ends of the orthopedic cable therethrough. The device is compressed/deformed at the time of placement, and then the device decompresses/springs back to substantially its original shape in response to time and/or a loss of tension in the orthopedic cable. The present disclosure is also directed to assemblies, systems, and kits that include this device, as well as methods of producing and using same, as described in greater detail herein below.

Certain non-limiting embodiments of the present disclosure are directed to a retension device for use with an orthopedic cable. The retension device includes at least two tensioning portions: a first tensioning portion having a first opening and a second opening extending therethrough, and a second tensioning portion having a first opening and a second opening extending therethrough. Each of the openings in the first and second tensioning portions is sized to allow the orthopedic cable to pass therethrough. The first openings of the first and second tensioning portions are substantially aligned, and the second openings of the first and second tensioning portions are substantially aligned; in this manner, a first section of the orthopedic cable can pass through the first openings, and a second section of the orthopedic cable can pass through the second openings. In this manner, the first openings of the first and second tensioning portions forms a first channel through which a first section of the orthopedic cable passes, while the second openings of the first and second tensioning portions form a second channel through which a second section of the orthopedic cable passes.

At least a portion of the retension device is formed of an elastic material.

The retension device is constructed in the form a clip or similarly constructed device that can assume a compressed form such that the first and second tensioning portions are compressed toward one another. The elastic material allows the retension device to decompress and increase a width of the first section of the orthopedic cable and a width of the second section of the orthopedic cable disposed between the first and second tensioning portions.

Any elastic materials known in the art or otherwise contemplated herein that are capable of functioning as described herein (i.e., compressing and decompressing in response to stimuli and/or time) and are safe for implantation within a subject may be utilized in producing a portion or all of the retension device. In certain non-limiting embodiments, the elastic material from which at least a portion of the retension device is formed comprises a shape memory material (such as, but not limited to, a shape memory alloy) or a spring steel.

When at least a portion of the retension device is formed of a shape memory material, the use of the shape memory material serves at least two functions. First, the elasticity of the shape memory material functions to allow for compression and decompression of the retension device. Second, the shape memory features of the shape memory material are activated upon implantation within the subject, as a body temperature of the subject is greater than an ambient temperature. The body temperature increases the temperature of the at least one shape memory material from which at least a portion of the retension device is formed, and this causes the compressed retension device to deform and move toward its original shape. Therefore, these two functions can work together to maintain tension on the orthopedic cable about which the retension device is disposed. Alternately, the material of the retension clip, such as (but not limited to) nitinol, can be processed so that the activation temperature thereof is around 0° C. In this manner, when the retension device is implanted in the body, the body's temperature instills even more energy to the retension device to expand from the compressed state.

In certain non-limiting embodiments, the shape memory material is a shape memory alloy, such as (but not limited to) alloys containing at least one of nickel, titanium, zinc, copper, gold, silver, platinum, aluminum, iron, manganese, gallium, tin, silicon, cadmium, cobalt, or palladium. Non-limiting examples of various shape memory alloys that can be utilized in accordance with the present disclosure are disclosed in U.S. Pat. No. 10,251,792.

In a particular (but non-limiting) embodiment, at least a portion of the device is formed of an elastic material that comprises a nickel-titanium alloy. One non-limiting example of a nickel-titanium alloy that can be utilized in accordance with the present disclosure is nitinol.

The first and second tensioning portions may be directly connected to one another. Alternatively, the retension device may further include one or more support portions that connect two tensioning portions to one another. For example (but not by way of limitation), the retension device may include one or more support portions that connects the first tensioning portion to the second tensioning portion. When present, at least a portion of the support portion is formed of the elastic material that compresses and decompresses to change the distance between the first and second tensioning portions.

In certain non-limiting embodiments, the retension device further includes one or more additional tensioning portions. For example (but not by way of limitation), the retension device may further include a third tensioning portion that is disposed between the first and second tensioning portions. The third tensioning portion contains first and second openings similar to those described for the first and second tensioning portions and through which the orthopedic cable can be passed through. The third tensioning portion (or additional tensioning portions) may be directly connected to one or more other tensioning portions and/or indirectly connected to one or more tensioning portions through a support portion.

The tensioning device may be provided with any shape, configuration, and/or dimensions that allow(s) the tensioning device to function in accordance with the present disclosure. For example (but not by way of limitation), the tensioning device may be provided with a substantially S-shaped configuration that comprises three planar sections and two convex sections. In the substantially S-shaped configuration, a first planar section defines the first tensioning portion, a first convex section defines a first support portion, a second planar section defines the second tensioning portion, a second convex section defines a second support portion, and a third planar section defines the third tensioning portion. The first convex section connects the first planar section to the third planar section, and the second convex section connects the second planar section to the third planar section.

In other non-limiting examples, the retension device has a substantially circular, oval, square, rectangular, hexagonal, octagonal, decagonal, or other polygonal shape that comprises two planar sections that are directly connected to one another or indirectly connected to one another via one or more support portions. In these embodiments, the first planar section defines the first tensioning portion, and the second planar section defines the second tensioning portion.

The first and second openings in the first and second tensioning portions of the retension device must each have a diameter sufficient to allow the orthopedic cable to pass therethrough. As such, the diameters of these openings will be dependent upon the particular orthopedic cable used therewith. Non-limiting examples of diameters that may be utilized in accordance with the present disclosure include about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, about 2.1 mm, about 2.2 mm, about 2.3 mm, about 2.4 mm, about 2.5 mm, about 2.6 mm, about 2.7 mm, about 2.8 mm, about 2.9 mm, about 3.0 mm, and the like, as well as a range of any of the above values (i.e., a range of from about 1.1 mm to about 1.8 mm, etc.).

Certain non-limiting embodiments of the present disclosure are directed to an assembly that includes one or more of any of the retension devices described or otherwise contemplated herein, in combination with an orthopedic cable. The orthopedic cable has a first end and a second end. The first openings in the first and second tensioning portions of the retension device form a first channel through which the first end of the orthopedic cable is passed through, while the second openings in the first and second tensioning portions of the retension device form a second channel through which the second end of the orthopedic cable is passed through. In this manner, a first section of the orthopedic cable is disposed between the first openings, and a second section of the orthopedic cable is disposed between the second openings.

Any orthopedic cable known in the art or otherwise contemplated herein may be utilized in accordance with the present disclosure. For example (but not by way of limitation), the orthopedic cable may be formed of any suitable implantable material, such as (but not limited to) stainless steel or cobalt-chrome materials. Particular non-limiting examples of materials from which the orthopedic cable may be formed include 316L stainless steel titanium alloy and L605 cobalt chromium alloy.

The orthopedic cable may be provided with any diameter and weave that allows the orthopedic cable to function in a cerclage system as described herein. That is, the diameter and weave of the orthopedic cable must provide sufficient flexibility to allow the cable to be passed/wrapped about bone while also providing sufficient strength to prevent breakage of the cable. Non-limiting examples of diameters that can be utilized in accordance with the present disclosure include about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, and the like, as well as a range of any of the above values (i.e., a range of from about 1.0 mm to about 1.7 mm, etc.). One non-limiting example of a weave that can be utilized in accordance with the present disclosure is an (8×7)+(1×19) weave.

In certain non-limiting embodiments, the second end of the orthopedic cable has an enlarged portion that cannot pass through the second openings in the first and second tensioning portions.

Orthopedic cables used in cerclage systems are well known in the art; therefore, no further discussion thereof is deemed necessary.

In certain non-limiting embodiments, the assembly further includes an inline crimp disposed on the orthopedic cable between the retension device and the first end of the orthopedic cable. Any crimps known in the art or otherwise contemplated herein for use with orthopedic cables in cerclage systems may be utilized in accordance with the present disclosure. For example (but not by way of limitation), the crimp may be formed of steel, titanium, cobalt-chromium, and combinations or alloys thereof. Crimps that are used with orthopedic cables are well known in the art; therefore, no further discussion thereof is deemed necessary.

The assembly may contain a single retension device or a plurality of retension devices. When multiple retension devices are present, the multiple retension devices may not be connected, or two or more of the retension devices may be connected to one another. For example (but not by way of limitation), it may be desirable for an assembly to include two or more retension devices that are daisy-chained to one another. In this manner, the amount of compression achieved can be increased and/or controlled, as desired.

Certain non-limiting embodiments of the present disclosure are directed to a system that includes one or more of any of the assemblies described herein above (and that contain at least one retension device, an orthopedic cable, and an inline crimp); in addition, the assembly, the system further includes at least one plate and/or at least one implant. In certain non-limiting embodiments, the system may include other components that aid in initial placement of the plate and/or implant, such as (but not limited to) one or more screws (such as, but not limited to, periprosthetic screws); one or more pins (such as, but not limited to, cerclage positioning pins or crimp positioning pins); one or more buttons (such as, but not limited to, cerclage buttons); or one or more wires (such as, but not limited to, Kirschner wires).

Certain non-limiting embodiments of the present disclosure are directed to a kit that contains one or more of any of the retension devices described or otherwise contemplated herein. The kit may include a single retension device or a plurality of retension devices. When a plurality of retension devices are present, the retension devices may have the same size and shape, or the devices may have two or more different sizes and/or shapes.

In certain non-limiting embodiments, the kit may further include one or more of any of the assembly or system components described herein. Non-limiting examples of these components include at least one segment of orthopedic cable; at least one inline crimp; at least one orthopedic plate; at least one periprosthetic implant; at least one pin; at least one button; at least one screw; and at least one wire.

In certain non-limiting embodiments, the kit may further include one or more instruments that are utilized in the formation and/or placement of any of the assemblies and/or systems described herein. Non-limiting examples of instruments that may be utilized in accordance with the present disclosure include a cable tensioner, a cable crimper, forceps, a cable cutter, a cable passer, an attachment bit (for attachment to the cable tensioner), a provisional tensioning device (for attachment to the cable tensioner), and any combinations thereof.

The relative numbers and amounts of retension device(s), orthopedic cable(s), inline crimp(s), orthopedic plate(s), implant(s), pin(s), button(s), wire(s), screw(s), and/or instrument(s) present in the kit can vary widely. Also, when a plurality of a particular component is present, the multiple components present may have the same shape and/or size, or the components may have two or more different shapes and/or sizes.

The different components may be present in the kit in any manner disclosed herein or otherwise known in the art. For example (but not by way of limitation), each of the components may be disposed in separate compartments, or two or more of the same or different components may be disposed in the same compartment. In addition, two or more of the components may be associated with one another prior to disposal within the kit. That is, the orthopedic cable may be threaded through the retension device(s) and/or the inline crimp prior to disposal within the kit.

In addition, the kit can further include a set of written instructions explaining how to use one or more components of the kit. A kit of this nature can be used in any of the methods described or otherwise contemplated herein.

Certain non-limiting embodiments of the present disclosure are directed to a method of treating a subject, in which any of the assemblies described or otherwise contemplated herein is disposed about at least a portion of a bone within the subject, and the assembly is secured in position thereabout. In a particular (but non-limiting) embodiment of the method, any of the assemblies described or otherwise contemplated herein is disposed about at least a portion of a plate disposed upon at least a portion of a bone within the subject, and the assembly is secured in position thereabout.

In certain non-limiting embodiments, the portion of bone about which the assembly is disposed comprises a fracture, such as (but not limited to), a periprosthetic fracture.

Certain non-limiting embodiments of the present disclosure are directed to a method of treating a subject. In the method, at least one plate or implant is affixed to a bone of the subject by disposing any of the assemblies described or otherwise contemplated herein about the bone, wherein the orthopedic cable is wrapped about the plate/implant and bone and then secured in place via the inline crimp.

Figure 2:
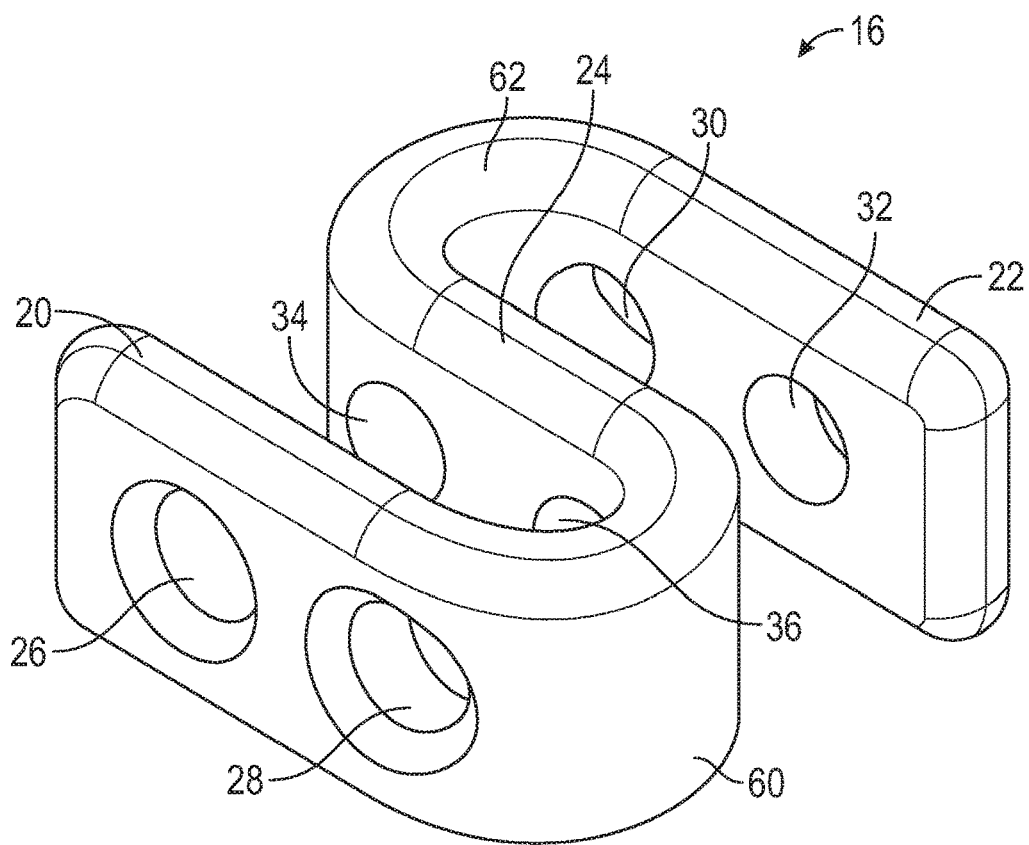
FIG. 2 is a perspective view of the retension device of FIG. 1.

Turning now to the Drawings, and in particular to FIG. 1, an assembly 10 that is constructed in accordance with the present disclosure is shown. The assembly 10 includes an orthopedic cable 12, a crimp 14, and a retension device 16. The retension device 16 (which is also illustrated in FIG. 2) includes three tensioning portions: a first tensioning portion 20, a second tensioning portion 22, and a third tensioning portion 24. The first tensioning portion 20 has a first opening 26 and a second opening 28 extending therethrough, wherein each opening 26 and 28 is sized to allow the orthopedic cable 12 to pass therethrough. The second tensioning portion 22 has a first opening 30 and a second opening 32 extending therethrough, wherein each opening 30 and 32 is sized to allow the orthopedic cable 12 to pass therethrough. The third tensioning portion 24 has a first opening 34 and a second opening 36 extending therethrough, wherein each opening 34 and 36 is sized to allow the orthopedic cable 12 to pass therethrough.

The first openings 26, 30, and 34 of the tensioning portions 20, 22, and 24, respectively, are substantially aligned, so as to form a channel through which the orthopedic cable 12 can pass. Similarly, the second openings 28, 32, and 36 of the tensioning portions 20, 22, and 24, respectively, are substantially aligned so as to form a channel through which the orthopedic cable 12 can pass. In this manner, a first section 40 of the orthopedic cable 12 can pass through the first openings 26, 30, and 34, and is defined as having a width that spans between the opening 26 and the opening 30. Similarly, a second section 42 of the orthopedic cable 12 can pass through the second openings 28, 32, and 36, and is defined as having a width that spans between the opening 28 and the opening 32.

The orthopedic cable 12 has a first end 44 and a second end 46. The second end 46 has an enlarged portion 48 that extends beyond the second opening 28 of the first tensioning portion 20 and that cannot pass through the second opening 28 (and thus cannot pass through the second openings 32 and 36). The cable 12 that extends beyond the second opening 32 of the second tensioning portion 22 is wound around in a substantially circular or oval shape and then inserted first through the first opening 26 of the first tensioning portion 20, then through the first openings 34 and 30 of the tensioning portions 24 and 22, respectively. In this manner, the orthopedic cable 12 extends through the set of first openings 26, 34, and 30 in the opposite direction as it extends through the set of second openings 32, 36, and 28. As such, when the first end 44 and/or second end 46 of the orthopedic cable 12 are pulled in an opposing direction to the other end, a circumference of the wound portion of the orthopedic cable 12 is reduced.

Figure 3:
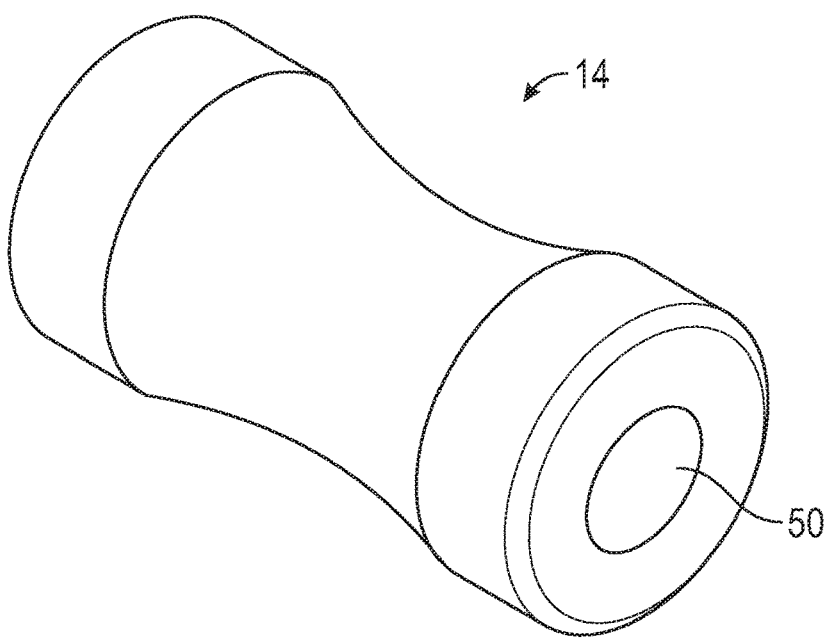
FIG. 3 is a perspective view of the crimp of FIG. 1.

The crimp 14 is attached to the portion of the orthopedic cable 12 that extends beyond the first opening 30 of the second tensioning portion 22 of the retension device 16 and secures that portion of the orthopedic cable 12. The crimp 14 is illustrated in greater detail in FIG. 3 and includes an opening 50 through which the orthopedic cable 12 extends. The crimp 14 is provided with at least one element within the opening 50 that secures the crimp 14 in place about the orthopedic cable 12 and prevents the crimp 14 and the retension device 16 from sliding along a length of the orthopedic cable 12.

At least a portion of the retension device 16 is formed of an elastic material that allows the retension device 16 to be initially compressed prior to or at the time of placement in a subject; this compression results in the first and second tensioning portions 20 and 22 being compressed toward one another. Over time and/or in response to the orthopedic cable 12 cutting into bone, at least a portion of the compression on the retension device 16 is released, and the first and second tensioning portions 20 and 22 move away from each other. This movement increases the widths of the first and second sections 40 and 42 of the orthopedic cable 12 and effectively reduces a circumference of the wound portion of the cable 12, thus increasing the tension that the assembly 10 exerts against other components about which the assembly 10 is positioned (see, for example, FIG. 9).

The entire retension device 16 may be formed of the elastic material, or only portion of the retension device 16 may be formed of the elastic material, while the other portions of the retension device 16 are formed of a non-elastic material, as described in greater detail herein below.

The tensioning portions 20, 22, and/or 24 may be directly connected to one another, or the retension device 16 may be provided with one or more support portions that connect two tensioning portions to one another. For example (but not by way of limitation), the retension device 16 is illustrated in FIGS. 1-2 as having an S-shaped configuration that comprises three planar sections and two convex sections, wherein the planar sections form tensioning portions, and the convex sections form support portions. That is, a first planar section defines the first tensioning portion 20, a first convex section defines a first support portion 60, a second planar section defines the third tensioning portion 24, a second convex section defines a second support portion 62, and a third planar section defines the second tensioning portion 22. In traversing the S-shape, the first support portion 60 connects the first tensioning portion 20 to the third tensioning portion 24, and the second support portion 62 connects the third tensioning portion 24 to the second tensioning portion 22 (FIG. 2).

At least a portion of the support portions 60 and 62 are formed of an elastic material that compresses and decompresses in response to time and/or stimuli; therefore, the support portions 60 and 62 participate in the compression of the retention device 16 so that the first and second tensioning portions 20 and 22 move toward one another. At least a portion of one or more of the tensioning portions 20, 22, and/or 24 may also be formed of an elastic material; alternatively, only the support portions 60 and 62 are formed of an elastic material, and the tensioning portion(s) are formed of a non-elastic material.

While the support portions 60 and 62 are illustrated as having a substantially convex shape, it will be understood that the support portions of any of the retention devices of the present disclosure may assume any shape and/or configuration that allows the support portion to function in accordance with the present disclosure. For example (but not by way of limitation), the support portions may assume shapes that are substantially convex, concave, planar, V-shaped, and the like. In addition, when two or more support portions are present, the support portions may have the same or different shapes and/or configurations.

While the retention device 16 is illustrated in FIGS. 1-2 as comprising the substantially S-shaped configuration that includes the support portions 60 and 62, it will be understood that the support portions need not be present. As such, the scope of the present disclosure also includes a retention device in which two or more tensioning portions are directly connected to one another and thus assume a substantially V-shape at the connection point between two tensioning portions. When no support portions are present, at least a portion of one of the tensioning portions must be formed of an elastic material.

Similarly, while the retention device 16 is illustrated as having three tensioning portions, it will be understood that the functions of the retention device can easily be accomplished with only two tensioning portions, or more than three tensioning portions; as such, retention devices with any number of tensioning portions also fall within the scope of the present disclosure.

While the retention device shown in FIGS. 1-2 is illustrated as having a substantially S-shaped configuration, this particular configuration is simply one non-limiting embodiment of the retention devices of the present disclosure. It will be understood that the retention devices produced in accordance with the present disclosure can assume any shape, size, and configuration, so long as the retention devices are capable of being present in the assemblies and systems disclosed herein and are capable of functioning in accordance with the present disclosure. For example (but not by way of limitation), FIGS. 4-8 illustrate several different shapes and configurations of retention devices, as described in greater detail herein below.

Figure 4:
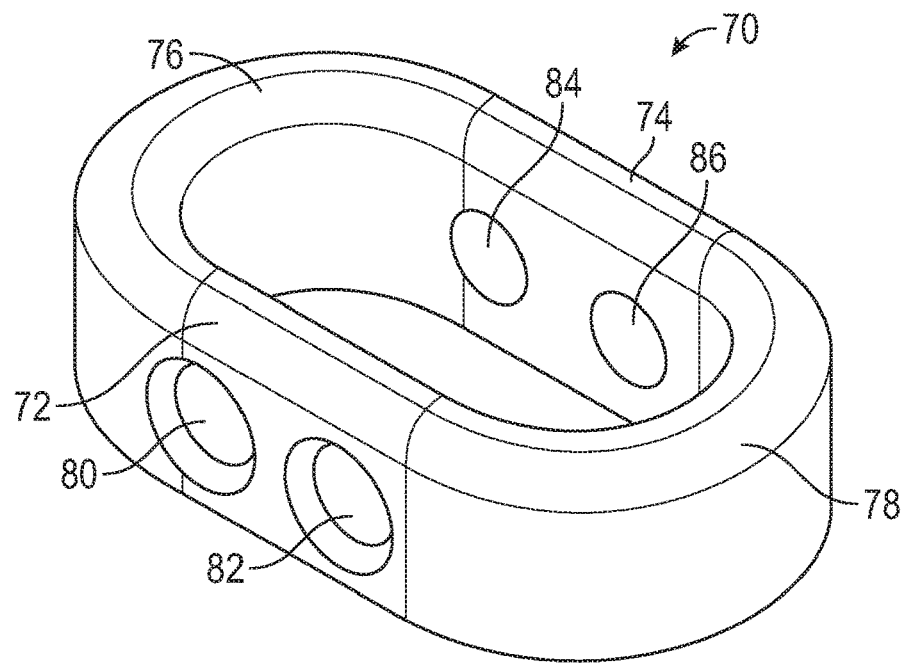
FIG. 4 is a perspective view of another non-limiting embodiment of a retension device constructed in accordance with the present disclosure.

FIG. 4 illustrates another embodiment of a retention device 70 that is similar to the retention device 16 of FIGS. 1-2, except as described herein below. The retention device 70 has a substantially oval or circular shape and includes a first tensioning portion 72, a second tensioning portion 74, a first support portion 76, and a second support portion 78. The support portions 76 and 78 each connect the first tensioning portion 72 to the second tensioning portion 74 to provide the circular or oval shape. The first tensioning portion 72 has a first opening 80 and a second opening 82, while the second tensioning portion 74 has a first opening 84 and a second opening 86. The tensioning portions, openings, and support portions function in the same manner as the corresponding tensioning portions, openings, and support portions of the retention device 10.

While the retention device 70 is illustrated as having a substantially circular or oval shape, it will be understood that the retention devices of the present disclosure can possess other shapes (such as (but not limited to) square, rectangular, hexagonal, octagonal, decagonal, or other polygonal shapes), so long as the retention device can compress and decompress so that at least two tensioning portions can move toward another during compression and away from one another (i.e., assume their original shape) during decompression.

Figure 5:
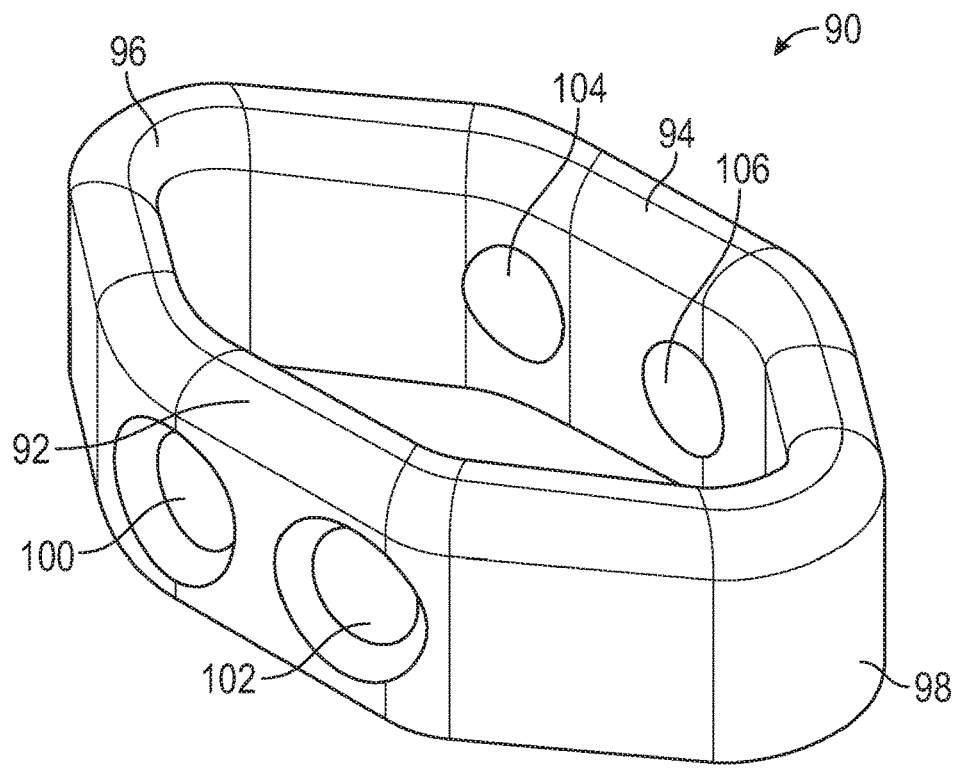
FIG. 5 is a perspective view of another non-limiting embodiment of a retension device constructed in accordance with the present disclosure.

For example (but not by way of limitation), FIG. 5 illustrates a retention device 90 that is similar to the retention devices 16 and 70 of FIGS. 1-2 and FIG. 4, respectively, except as described herein below. The retention device 90 has a substantially hexagonal shape and includes a first tensioning portion 92, a second tensioning portion 94, a first support portion 96, and a second support portion 98. The support portions 96 and 98 each possess a substantially U- or V-shape, and each of the support portions 96 and 98 connects the first tensioning portion 92 to the second tensioning portion 94 to provide the substantially hexagonal shape. The first tensioning portion 92 has a first opening 100 and a second opening 102, while the second tensioning portion 94 has a first opening 104 and a second opening 106. The tensioning portions, openings, and support portions function in the same manner as the corresponding tensioning portions, openings, and support portions of the retention devices 10 and 70.

Figure 6:
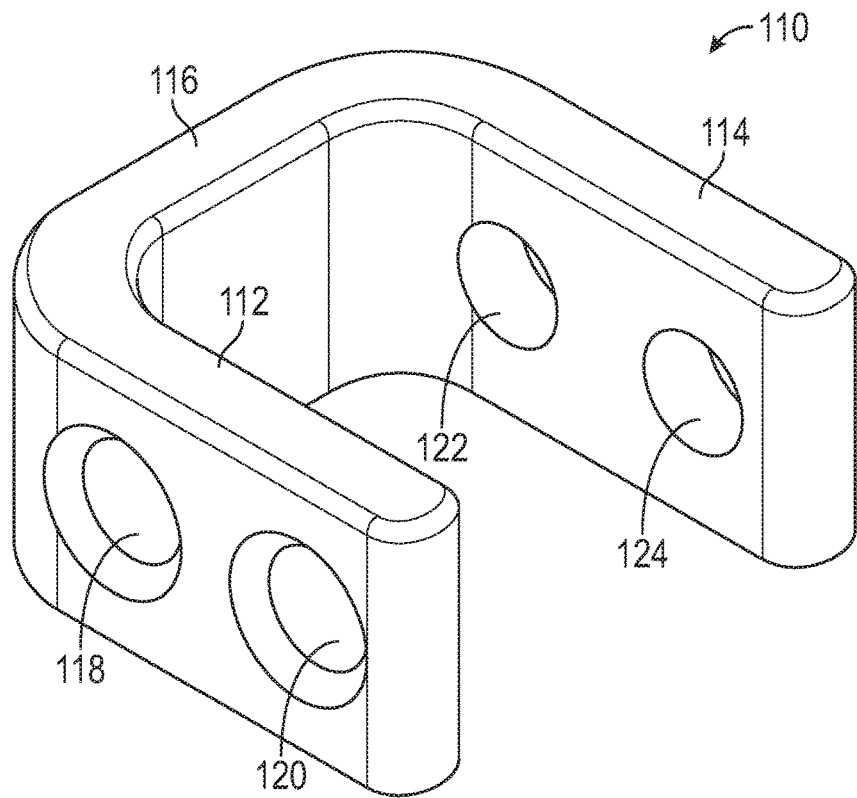
FIG. 6 is a perspective view of another non-limiting embodiment of a retension device constructed in accordance with the present disclosure.

FIG. 6 illustrates a retention device 110 that is similar to the retention device 16 of FIGS. 1-2, except as described herein below. While the retention device 16 has an S-shape that includes three tensioning portions and two support portions, the retention device 110 has a substantially bracketed or U-shape that includes only two tensioning portions attached by a single support portion. The retention device 110 includes a first tensioning portion 112 and a second tensioning portion 114 that are connected to one another via a support portion 116. The first tensioning portion 112 has a first opening 118 and a second opening 120, while the second tensioning portion 114 has a first opening 122 and a second opening 124. The tensioning portions, openings, and support portions function in the same manner as the corresponding tensioning portions, openings, and support portions of the previously described retention devices.

Figure 7:
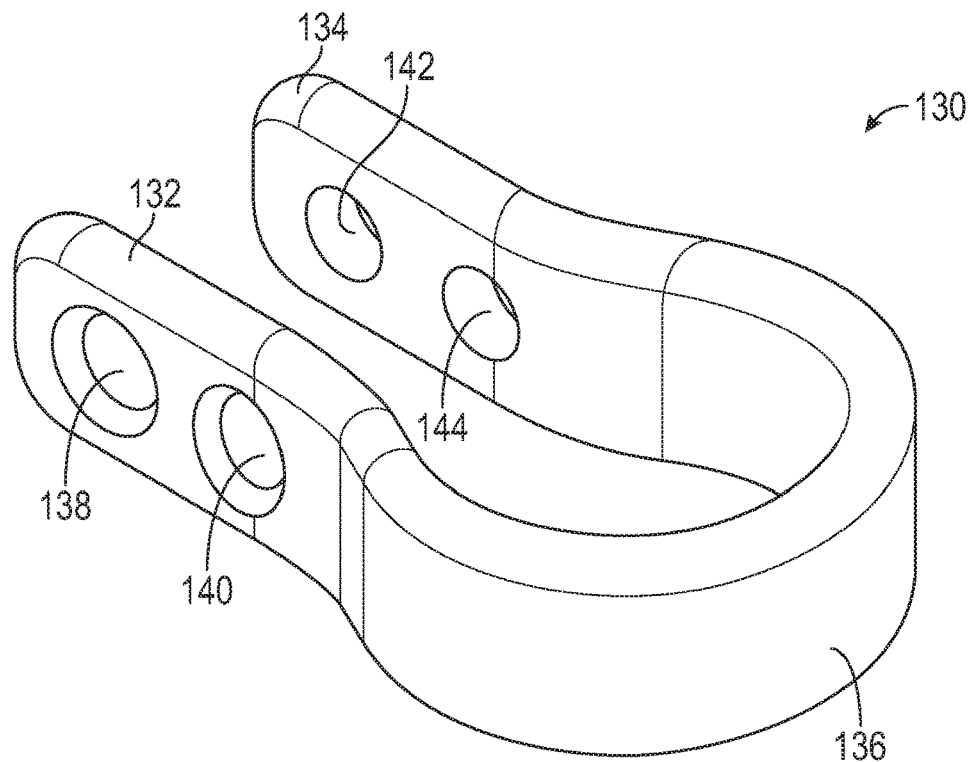
FIG. 7 is a perspective view of yet another non-limiting embodiment of a retension device constructed in accordance with the present disclosure.

FIG. 7 illustrates a retention device 130 that is similar to the retention device 110 of FIG. 6, except that the support portions of the two retention devices differ in configuration (substantially planar for the retention device 110 and substantially convex/horseshoe-shaped for the retention device 130). The retention device 130 includes a first tensioning portion 132 and a second tensioning portion 134 that are connected via a support portion 136 that is substantially horseshoe-shaped. The first tensioning portion 132 has a first opening 138 and a second opening 140, while the second tensioning portion 134 has a first opening 142 and a second opening 144. The tensioning portions, openings, and support portions function in the same manner as the corresponding tensioning portions, openings, and support portions of the previously described retention devices.

Figure 8:
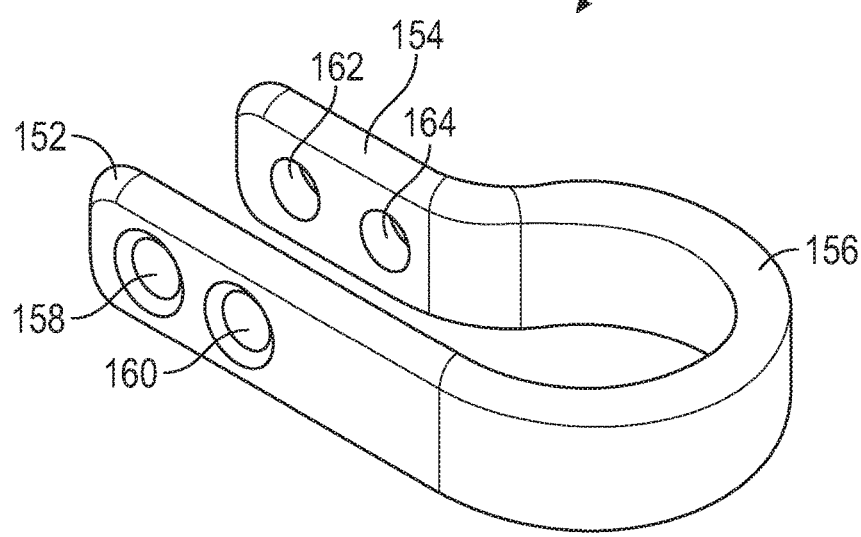
FIG. 8 is a perspective view of a further non-limiting embodiment of a retension device constructed in accordance with the present disclosure.

FIG. 8 illustrates a retention device 150 that is similar to the retention device 130 of FIG. 7, except that the support portion thereof has a slightly different configuration. The retention device 150 includes a first tensioning portion 152 and a second tensioning portion 154 that are connected to one another via a support portion 156. The first tensioning portion 152 has a first opening 158 and a second opening 160, while the second tensioning portion 154 has a first opening 162 and a second opening 164. The tensioning portions, openings, and support portions function in the same manner as the corresponding tensioning portions, openings, and support portions of the previously described retension devices.

In one non-limiting embodiment, the asymmetrical shape between the first and second tensioning portions 152 and 154 allows the device to be more easily connected in series, as two opposing tensioning portions 152 can be placed back to back.

While FIGS. 1-2 and 4-8 illustrate several different shapes, sizes, and configurations of retension devices, it will be understood that these different shapes/sizes/configurations are provided for purposes of example only. The retension devices of the present disclosure may assume any shapes/sizes/configurations contemplatable by a person having ordinary skill in the art, so long as the retension devices can function in the manner described herein; as such, all contemplatable shapes/sizes/configurations of retension devices fall within the scope of the present disclosure.

Figure 9:
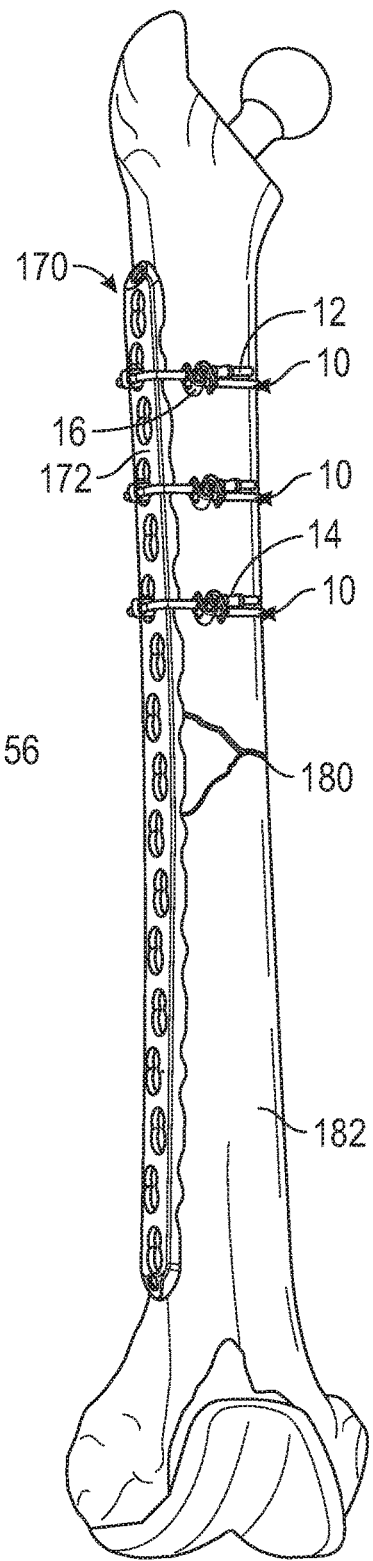
FIG. 9 is a perspective view of a system that includes a plurality of the assemblies of FIG. 1, wherein the system is utilized to set a periprosthetic fracture.

FIG. 9 illustrates a system 170 that is utilized to set a periprosthetic fracture 180 in a bone 182. The system 170 includes a plurality of any of the assemblies described or otherwise contemplated herein. For the purposes of illustration only, the system 170 is illustrated as including a plurality of the assemblies 10 of FIG. 1. The system 170 also includes a plate 172 that is disposed adjacent the bone 182 and spans a length of the bone 182 that includes the periprosthetic fracture 180. The plurality of assemblies 10 function to secure the plate 172 about the bone 182 so as to maintain the fractured portions of bone in the proper position for healing. As the orthopedic cable 12 of each assembly 10 begins to cut into the bone, the retension device 16 decreases the circumference of the orthopedic cable 12 of the assembly 10 and thus automatically retensions the orthopedic cable 12 of the assembly 10 about the bone 180 so as to retain the plate 172 in a secure position about the bone 180.

The system 170 may further include other components, such as (but not limited to) implants and/or components for securing the two portions of the fractured bone 180 to one another and/or for securing the plate 172 to the two portions of bone 180. The use of these types of components with currently available orthopedic cables are well known in the art, and thus no further description or illustration thereof is deemed necessary for the understanding of the full scope of the present disclosure.

Thus, in accordance with the present disclosure, there have been provided devices, assemblies, systems, and kits, as well as methods of producing and using same, which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

What is claimed is:

1. A retension device for use with an orthopedic cable, the retension device comprising:
   a first tensioning portion having a first opening and a second opening extending therethrough, wherein each opening is sized to allow the orthopedic cable to pass therethrough;
   a second tensioning portion having a first opening and a second opening extending therethrough, wherein each opening is sized to allow the orthopedic cable to pass therethrough;
   wherein the first openings of the first and second tensioning portions are substantially aligned, and the second openings of the first and second tensioning portions are substantially aligned, whereby a first section of the orthopedic cable can pass through the first openings, and a second section of the orthopedic cable can pass through the second openings; and
   wherein at least a portion of the retension device is formed of an elastic material, and wherein the retension device is provided in an initially compressed form such that the first and second tensioning portions are compressed toward one another, and wherein the elastic material allows the retension device to decompress and increase a width of the first section of the orthopedic cable and a width of the second section of the orthopedic cable disposed between the first and second tensioning portions.

2. The retension device of claim 1, wherein the elastic material comprises a shape memory alloy.

3. The retension device of claim 2, wherein the nickel-titanium alloy is nitinol.

4. The retension device of claim 1, further comprising at least one support portion that connects the first tensioning portion to the second tensioning portion, and wherein the support portion is formed of the elastic material that compresses and decompresses to change the distance between the first and second tensioning portions.

5. The retension device of claim 1, further comprising a third tensioning portion disposed between the first and second tensioning portions.

6. The retension device of claim 5, further defined as comprising an S-shaped configuration that comprises three planar sections and two convex sections, wherein a first planar section defines the first tensioning portion, a first convex section defines a first support portion, a second planar section defines the second tensioning portion, a second convex section defines a second support portion, and a third planar section defines the third tensioning portion, wherein the first convex section connects the first planar section to the third planar section, and wherein the second convex section connects the second planar section to the third planar section.

7. The retension device of claim 1, further defined as comprising a substantially circular, oval, square, rectangular, hexagonal, octagonal, decagonal, or polygonal shape that comprises two planar sections connected by two convex sections, and wherein the first planar section defines the first tensioning portion, and the second planar section defines the second tensioning portion.

8. An assembly comprising: a retension device for use with an orthopedic cable, the retension device comprising first and second tensioning portions that each have a first opening and a second opening extending therethrough, wherein the first openings of the first and second tensioning portions are substantially aligned, and the second openings of the first and second tensioning portions are substantially aligned, and wherein at least a portion of the retension device is formed of an elastic material; and
   an orthopedic cable having a first end and a second end, wherein the first end of the orthopedic cable is passed through the first openings in the first and second tensioning portions of the retension device, and wherein the second end of the orthopedic cable is passed through the second openings in the first and second tensioning portions of the retension device, whereby a first section of the orthopedic cable is disposed between the first openings, and a second section of the orthopedic cable is disposed between the second openings, wherein the elastic material allows the retension device to decompress and increase a width of the first section of the orthopedic cable and a width of the second section of the orthopedic cable disposed between the first and second tensioning portions.

9. The assembly of claim 8, wherein the second end of the orthopedic cable has an enlarged portion that cannot pass through the second openings in the first and second tensioning portions.

10. The assembly of claim 9, further comprising an inline crimp disposed on the orthopedic cable between the retension device and the first end of the orthopedic cable.

11. The assembly of claim 8, wherein the elastic material of the retension device comprises a shape memory alloy.

12. The assembly of claim 11, wherein the nickel-titanium alloy is nitinol.

13. The assembly of claim 8, wherein the retension device further comprises at least one support member that connects the first tensioning portion to the second tensioning portion.

14. The assembly of claim 8, further comprising a third tensioning portion.

* * * * *